United States Patent
Hodrinsky et al.

(10) Patent No.: US 12,285,220 B1
(45) Date of Patent: Apr. 29, 2025

(54) SYSTEM AND METHOD FOR PLANNING AND SIMULATING A SURGICAL OPERATION TO CREATE A PATIENT-SPECIFIC SPINAL IMPLANT

(71) Applicants: Todd W Hodrinsky, Mansfield Center, CT (US); Marcel Janse, Mansfield Center, CT (US)

(72) Inventors: Todd W Hodrinsky, Mansfield Center, CT (US); Marcel Janse, Mansfield Center, CT (US)

(73) Assignee: NIVALON MEDICAL TECHNOLOGIES INC., Mansfield Center, CT (US)

(*) Notice: Subject to any disclaimer, the term of this patent is extended or adjusted under 35 U.S.C. 154(b) by 0 days.

(21) Appl. No.: 18/824,839

(22) Filed: Sep. 4, 2024

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/25* (2016.02); *A61F 2/30942* (2013.01);
(Continued)

(58) Field of Classification Search
CPC ... A61B 34/10; A61B 34/25; A61B 2034/102; A61B 2034/105; A61B 2034/258;
(Continued)

(56) References Cited

U.S. PATENT DOCUMENTS

| | | | |
|---|---|---|---|
| 11,553,969 B1 * | 1/2023 | Lang | G02B 27/0172 |
| 2023/0255690 A1 * | 8/2023 | Castro | A61B 34/10 623/11.11 |
| 2023/0270562 A1 * | 8/2023 | Roh | G16H 30/40 606/1 |

FOREIGN PATENT DOCUMENTS

WO WO-2023076717 A2 * 5/2023 ............. A61B 34/10

OTHER PUBLICATIONS

X. Li, A. Heidari, S.M. Nourbakhsh, R. Mohammadi, D. Semiromi, Design and fabrication of elastic two-component polymer-metal disks using a 3D printer under different loads for the lumbar spine, Polymer Testing, vol. 112, 2022, 12 pages. (Year: 2022).*

* cited by examiner

*Primary Examiner* — Karlheinz R. Skowronek
*Assistant Examiner* — Emilie A Neulen
(74) *Attorney, Agent, or Firm* — Sam Pierce

(57) ABSTRACT

A system and method for planning and simulating a surgical operation to create a patient-specific spinal implant are disclosed. The system comprises a remote server configured to receive patient-specific medical image data and generate a 3D mesh model of the patient's spine using algorithms that separate vertebral bodies, remove artifacts, and smooth surfaces. A doctor's computer receives the 3D mesh model and allows real-time manipulation of intervertebral spaces to achieve a desired spinal curvature. The server generates a spinal implant design with surface-mapped endplates matching the patient's vertebral anatomy, which is transmitted to a 3D printer for manufacturing. The method includes steps of receiving image data, generating and updating the 3D mesh model based on doctor input, generating the final implant design, and transmitting it for production. The invention enables the creation of patient-specific spinal implants with improved conformity and surgical outcomes.

11 Claims, 3 Drawing Sheets

(51) Int. Cl.
*A61F 2/30* (2006.01)
*A61F 2/46* (2006.01)
(52) U.S. Cl.
CPC ... *A61B 2034/102* (2016.02); *A61B 2034/105* (2016.02); *A61B 2034/258* (2016.02); *A61F 2002/30948* (2013.01); *A61F 2002/30953* (2013.01); *A61F 2002/30955* (2013.01); *A61F 2002/30985* (2013.01); *A61F 2/4611* (2013.01)
(58) Field of Classification Search
CPC .............. A61F 2/30942; A61F 2/4611; A61F 2002/30948; A61F 2002/30953; A61F 2002/30955; A61F 2002/30985
See application file for complete search history.

SYSTEM AND METHOD FOR PLANNING AND SIMULATING A SURGICAL OPERATION TO CREATE A PATIENT-SPECIFIC SPINAL IMPLANT

BACKGROUND OF THE INVENTION

Field of Invention

The various aspects discussed herein relate to systems and methods for designing and manufacturing patient-specific spinal implants.

Description of Related Art

Spinal implants are used to correct spinal defects, restore alignment, and alleviate pain in patients suffering from various spinal conditions. However, there are problems with existing spinal implants and the processes used to design and manufacture them. Conventional spinal implants often fail to precisely match the unique anatomy of each patient's spine, leading to suboptimal outcomes. Furthermore, the design process typically involves multiple steps and can be time-consuming, requiring extensive collaboration between doctors and implant manufacturers.

Accordingly, there is a need in the art for an improved system and method for designing and manufacturing patient-specific spinal implants that addresses these problems. Such a system would enable doctors to manipulate a 3D model of the patient's spine in real-time, adjusting the spacing, tilt, and angles of the vertebrae to achieve the desired curvature. The resulting implant design would feature surface-mapped endplates that precisely match the patient's vertebral anatomy, ensuring an optimal fit. By streamlining the design and manufacturing process through the use of advanced imaging, 3D modeling, and 3D printing technologies, the system would reduce lead times and improve patient outcomes.

BRIEF SUMMARY OF THE INVENTION

This summary is provided to introduce a selection of concepts, in a simplified format, that are further described in the detailed description of the invention. This summary is neither intended to identify key or essential inventive concepts of the invention nor is it intended for determining the scope of the invention.

The present invention provides a comprehensive system and method for designing and manufacturing patient-specific spinal implants. The system comprises a remote server that receives patient medical imaging data and converts it into a manipulatable 3D mesh model of the spine using a novel algorithm. The algorithm automatically separates individual vertebrae, removes artifacts, and smooths surfaces to generate a clean, accurate model.

In one embodiment, a doctor can access the 3D model via a secure connection to the remote server and use a computer interface to adjust the spacing, tilt, angles, and curvature of the vertebrae to correct defects and optimize alignment. The interface provides intuitive tools for the doctor to visualize and fine-tune the model in real-time. The system then generates a spinal implant design with surface-mapped endplates that precisely match the patient's unique vertebral anatomy, ensuring an optimal fit and improved surgical outcomes compared to conventional implants.

Advantageously, the system streamlines the implant design process by enabling seamless collaboration between the doctor and the modeling software, reducing the turnaround time from patient imaging to implant manufacturing. The resulting patient-specific implants, which may feature a solid or flexible core, provide superior conformity and biomechanical performance.

In operation, the system's 3D modeling and printing capabilities allow for rapid iteration and production of implants on-demand, reducing lead times and enhancing flexibility compared to traditional manufacturing. Furthermore, the system's secure, encrypted data transmission and HIPAA-compliant storage ensure the protection of sensitive patient information.

Additional features and advantages of the invention will be set forth in the description which follows. These and other features of the present invention will become more fully apparent from the following description, or may be learned by the practice of the invention as set forth hereinafter.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION

Figure 1:
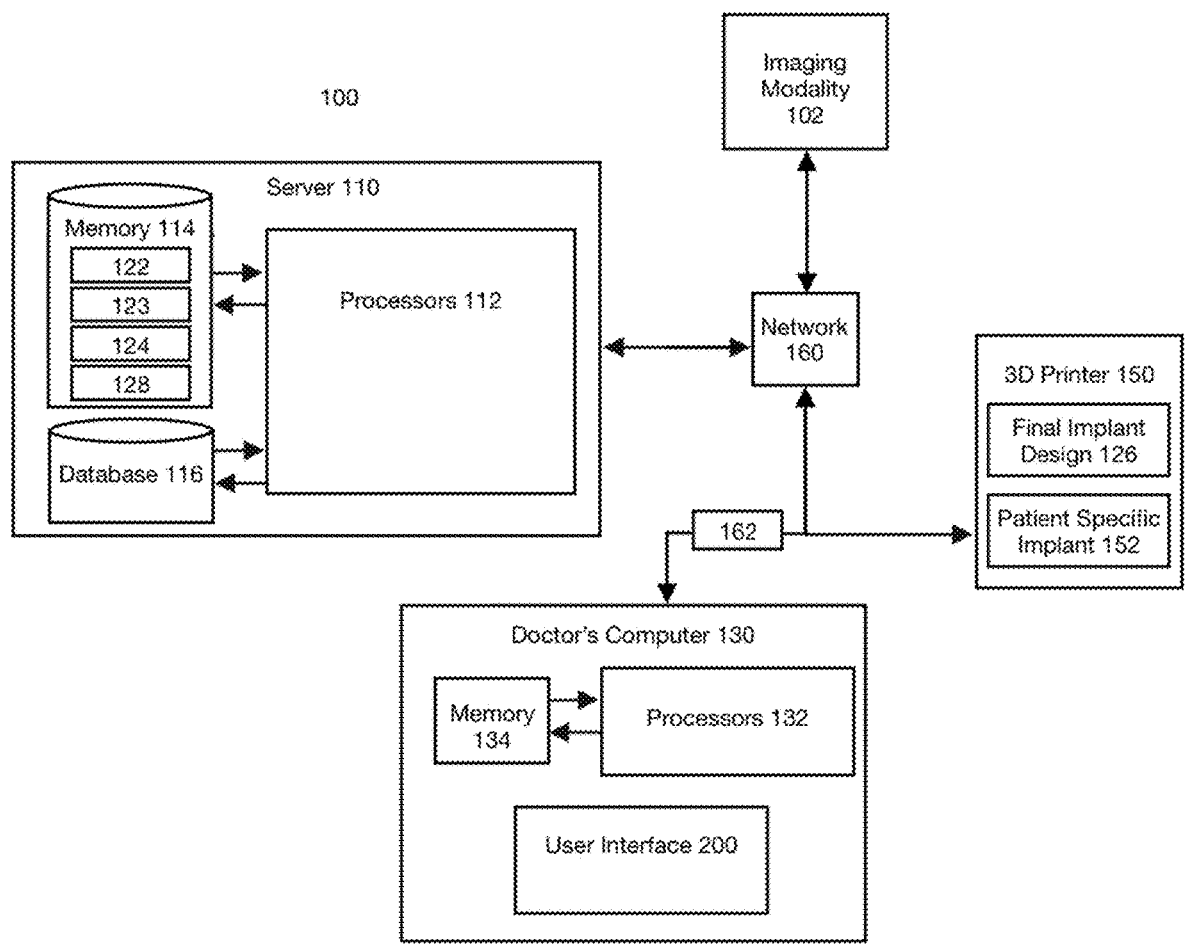
FIG. 1 is a system block diagram illustrating the components and interactions of a computer-implemented system for planning and simulating a surgical operation to create a patient-specific spinal implant, according to one embodiment of the present invention.

In the following detailed description of the preferred embodiments, reference is made to the accompanying drawings, which form a part hereof and show, by way of illustration, specific embodiments in which the invention may be practiced. It is to be understood that other embodiments may be used and structural or logical changes may be made without departing from the scope of the present invention. The following detailed description, therefore, is not to be taken in a limiting sense, and the scope of the present invention is defined by the appended claims.

The following description is provided as an enabling teaching of the present systems, and/or methods in its best, currently known aspect. To this end, those skilled in the relevant art will recognize and appreciate that many changes can be made to the various aspects of the present systems described herein, while still obtaining the beneficial results of the present disclosure. It will also be apparent that some of the desired benefits of the present disclosure can be obtained by selecting some of the features of the present disclosure without utilizing other features.

Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

The terms "a" and "an" and "the" and similar references used in the context of describing a particular embodiment of the present invention (especially in the context of certain claims) are construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein.

All systems described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application. Thus, for example, reference to "an element" can include two or more such elements unless the context indicates otherwise.

As used herein, the terms "optional" or "optionally" mean that the subsequently described event or circumstance can or cannot occur, and that the description includes instances where said event or circumstance occurs and instances where it does not.

The word or as used herein means any one member of a particular list and also includes any combination of members of that list. Further, one should note that conditional language, such as, among others, "can," "could," "might", or "may" unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular aspect.

FIG. 1 is a system block diagram illustrating the components and interactions of a computer-implemented system (100) for planning and simulating a surgical operation to create a patient-specific spinal implant, according to one embodiment of the present invention. In one embodiment, the system (100) may comprise a remote server (110), a doctor's computer (130), and a 3D printer (150) interconnected via a data communications network (160), such as, by way of example and not limitation, the Internet or a private network like a virtual private network (VPN), wherein the network (160) can enable secure, encrypted data transfer between the system components using protocols including but not limited to Transport Layer Security (TLS) or Internet Protocol Security (IPsec). For example, the network (160) might employ end-to-end encryption using a cipher such as a 256-bit Advanced Encryption Standard (AES-256) cipher to protect sensitive patient data transmitted between the remote server (110) and the doctor's computer (130).

As shown in FIG. 1, the remote server (110) generally includes one or more processors (112), such as, by way of example and not limitation, Intel Xeon or AMD Epyc server-grade CPUs, and a memory (114), which may comprise a combination of random-access memory (RAM) and non-volatile storage such as solid-state drives (SSDs) or hard disk drives (HDDs). The memory (114) can include high-speed RAM modules, such as DDR4 or DDR5 RAM modules, for rapid data access and processing, as well as enterprise-grade SSDs with interfaces including but not limited to NVMe interfaces for reliable, low-latency storage of the patient data and system software. According to an embodiment, the one or more processors (112) are configured to receive patient-specific medical image data from an imaging modality (102), including but not limited to a magnetic resonance imaging (MRI) scanner, computed tomography (CT) scanner, or a three-dimensional (3D) surface scanning system such as a structured light or laser scanner. The imaging modality (102) may be directly coupled to the remote server (110) via a high-speed, low-latency interface such as, by way of example and not limitation, Gigabit Ethernet or Thunderbolt, or it may transfer the image data to the server (110) through the network (160) using a secure, encrypted connection. The received image data, which can be in a standard medical imaging format such as DICOM (Digital Imaging and Communications in Medicine), is stored in a secure database (116) on the server (110), wherein the database (116) may be implemented using a database management system such as a relational database management system (RDBMS) like MySQL, PostgreSQL, or Microsoft SQL Server, or a NoSQL database such as MongoDB or Couchbase. The database (116) can be configured with redundancy and failover mechanisms, such as, by way of example and not limitation, RAID storage or database replication, to ensure data integrity and availability.

In another embodiment, the one or more processors (112) execute a first image processing algorithm (123) stored in the memory (114) to generate a 3D mesh model of the patient's spine from the acquired image data. The first algorithm (123) stored in the memory (114), can be implemented using high-performance computing frameworks such as CUDA or OpenCL to leverage the parallel processing capabilities of modern GPUs, thereby accelerating the computationally intensive tasks involved in generating the 3D mesh model. The first algorithm performs several pre-processing steps to enhance the quality and usability of the image data for subsequent modeling. These steps may include, but are not limited to:

1. Automatically detecting and removing unwanted artifacts and noise using a secondary filtering algorithm based on techniques such as, by way of example and not limitation, median filtering, Gaussian smoothing, or anisotropic diffusion, wherein, for example, streak artifacts in CT scans caused by metallic implants can be significantly reduced using a metal artifact reduction (MAR) algorithm. The MAR algorithm may employ advanced techniques including but not limited to projection interpolation, normalization, or iterative reconstruction to suppress metal artifacts while substantially preserving the underlying anatomical details.

2. Smoothing the surfaces of the segmented vertebral bodies using methods such as, by way of example and not limitation, Laplacian smoothing or Taubin smoothing to reduce staircase artifacts and create more anatomically realistic models.

3. Separating the individual vertebral bodies for independent manipulation by applying image segmentation techniques such as, by way of example and not limitation, thresholding, region growing, or active contours, wherein each vertebra is assigned a unique label or identifier to facilitate subsequent referencing and selection. The segmentation process may be guided by a priori knowledge of the spinal anatomy, such as the expected size, shape, and position of each vertebra, to improve the accuracy and robustness of the segmentation results.

4. Creating reference lines and connection points on the vertebral models to aid in the placement and orientation of the spinal implant, wherein these may include, but are not limited to, anatomical landmarks such as the pedicles, transverse processes, or superior and inferior endplates. These reference features can be automatically detected using machine learning algorithms trained on a large dataset of annotated spinal images, or they may be manually defined by the doctor using an interactive user interface (200).

The resulting 3D mesh model can include individual vertebral bodies and intervertebral spaces represented as a high-resolution polygon mesh, such as, by way of example and not limitation, a triangular or quadrilateral mesh, defining the surface geometry of the vertebrae, wherein the polygon mesh data structure allows for efficient manipulation and rendering of the complex vertebral shapes. The mesh resolution may be adaptively adjusted based on the complexity of the vertebral geometry, with higher resolutions used for areas with fine details or high curvature, and lower resolutions used for smoother, less complex regions to optimize storage and processing efficiency. In one embodiment, the generated model is transmitted via the network (160) to the doctor's computer (130) for real-time manipulation using a secure, encrypted connection (162) such as, but not limited to, a VPN tunnel with AES-256 encryption or a TLS/SSL connection.

As depicted in FIG. 1, the doctor's computer (130) also comprises one or more processors (132), such as, by way of example and not limitation, high-performance Intel Core or AMD Ryzen CPUs, and a memory (134) for storing program instructions and data. The memory (134) may include a combination of high-speed RAM and fast, reliable storage such as an NVMe SSD to ensure smooth, responsive performance of the interactive user interface (200). In another embodiment, the one or more processors (132) are configured to display the 3D mesh model on the interactive user interface (200), such as, but not limited to, a web-based application or a dedicated desktop software, thereby allowing the doctor to adjust the spacing, tilt, and angles of one or more intervertebral spaces to achieve a desired spinal curvature and alignment. The user interface (200) may be implemented using modern web technologies like HTML5, WebGL, and JavaScript, or using cross-platform frameworks like Qt or Electron, to provide a rich, interactive 3D visualization and manipulation environment that is accessible from a wide range of devices and operating systems.

In one embodiment, the doctor can interact with the model using various intuitive tools provided in the interface (200). These tools may include, but are not limited to:

1. Toggles to control the visibility and transparency of individual vertebral bodies, thereby allowing the doctor to focus on specific regions of interest or visualize the spatial relationships between vertebrae. These toggles may be implemented as, by way of example and not limitation, checkboxes, sliders, or buttons that directly manipulate the rendering properties of the corresponding mesh elements in real-time.
2. Warning indicators that highlight potentially problematic adjustments, such as, but not limited to, excessive lordosis or kyphosis, or collision between adjacent vertebrae, wherein these indicators may be implemented as color-coded overlays on the model or as textual alerts. The warning system may be based on a set of predefined rules or thresholds derived from expert knowledge or statistical analysis of a large dataset of healthy and pathological spinal curvatures.
3. Grabbing and manipulating tools to adjust segments or groups of segments and immediately view the impact on adjacent levels, wherein the doctor can select vertebrae using a mouse, or a touchscreen, and apply translations or rotations to simulate different surgical maneuvers. These tools may employ intuitive gesture-based interfaces, such as, but not limited to, click-and-drag or pinch-to-zoom, to provide a natural and efficient way of interacting with the 3D model.
4. Measurement tools to quantify the distances, angles, and alignments between vertebrae and assess the biomechanical properties of the spine, wherein, for example, the Cobb angle, which is commonly used to evaluate spinal curvature, can be automatically calculated and displayed based on the adjusted model. Other relevant measurements, such as, but not limited to, the sagittal vertical axis (SVA), pelvic incidence (PI), pelvic tilt (PT), and sacral slope (SS), may also be computed and visualized to provide a comprehensive assessment of the spinal alignment and balance.
5. Cross-sectional and multi-planar viewing options to visualize the spinal anatomy from different perspectives, wherein traditional 2D radiographic views like anterior-posterior (AP) and lateral views can be generated from the 3D model and displayed alongside the 3D rendering for reference. These views may be automatically updated in real-time as the doctor adjusts the 3D model, providing a synchronized, multi-modal visualization of the spinal anatomy and the planned surgical outcome.

According to an embodiment, once the doctor has finished manipulating the 3D mesh model (122) to achieve the desired surgical plan, the updated model is transmitted back to the remote server (110) via the secure network connection (162). The secure network connection (162) may employ industry-standard encryption protocols, such as Transport Layer Security (TLS) or Internet Protocol Security (IPsec), to protect the confidentiality and integrity of the transmitted data. Additionally, the connection (162) may utilize virtual private network (VPN) technology to establish a secure, encrypted tunnel between the doctor's computer (130) and the remote server (110), ensuring that the sensitive patient information and surgical planning data are shielded from unauthorized access or interception.

The one or more processors (112) on the server then execute additional algorithms (128) stored in the memory (114) to generate a final 3D spinal implant design (126) based on the updated model (124). These algorithms may leverage advanced computational geometry and computer-aided design (CAD) techniques, such as non-uniform rational B-spline (NURBS) modeling, constructive solid geometry (CSG), or parametric modeling, to create a precise, manufacturable implant design that conforms to the patient's unique spinal anatomy and the planned surgical outcome. The algorithms may also incorporate finite element analysis (FEA) methods to optimize the implant design for strength, durability, and biomechanical compatibility, ensuring that the final implant can withstand the expected loads and stresses within the patient's spine.

In one embodiment, the final implant design (126) comprises surface-mapped endplates that precisely match the unique anatomy of the patient's specific vertebral bodies, as determined from the updated 3D mesh model (124). The surface mapping process may involve advanced geometric algorithms, such as point cloud registration, surface reconstruction, or mesh deformation, to create a smooth, continuous interface between the implant and the vertebral endplates. This precise matching ensures optimal load transfer and stability between the implant and the surrounding bone, promoting successful fusion and reducing the risk of implant subsidence or migration.

The design may include either a fusion cage with a solid core or a flexible core implant, depending on the doctor's selection in the interface (200). The choice between a fusion cage and a flexible core implant may be based on factors comprising the patient's age, bone quality, spinal stability, and the specific surgical goals. Fusion cages are typically indicated for patients requiring a solid, stable construct to promote bony fusion, while flexible core implants are often used in cases where preserving some degree of motion and flexibility is desirable, such as in younger patients or those with less severe degenerative changes.

Figure 2:
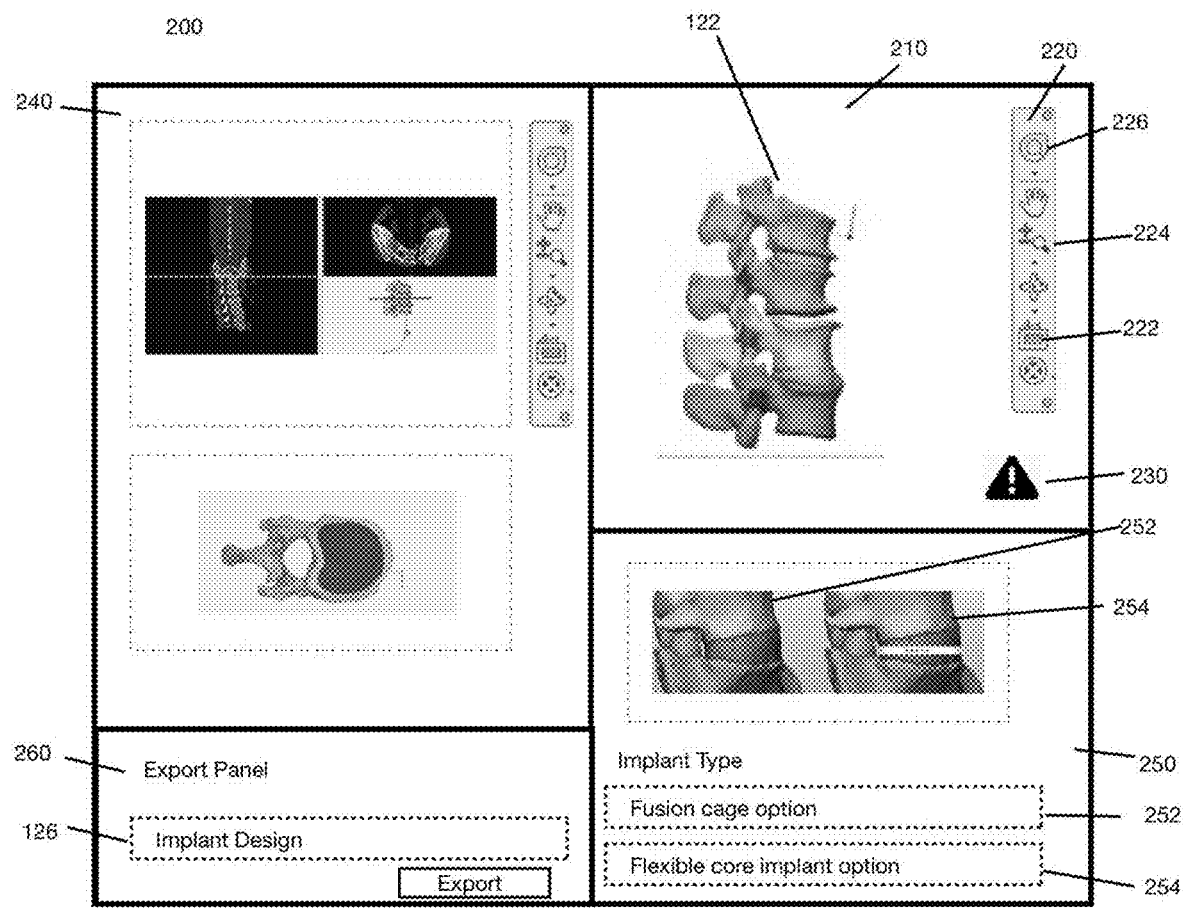
FIG. 2 illustrates a user interface (UI) of the computer-implemented system for planning and simulating a surgical operation to create a patient-specific spinal implant, according to one embodiment of the present invention.

As shown in FIG. 1-2, for a fusion cage embodiment, the algorithm generates an extrusion base template from the surface-mapped endplates to form a flat parallel surface or solid extrusion profile matching the vertebral body surfaces, wherein the cage design may incorporate additional features like porous scaffolds or bioactive coatings to promote osseointegration and improve fusion rates. These scaffolds provide a favorable environment for bone ingrowth and vascularization, enhancing the biological fixation of the implant. Bioactive coatings, such as hydroxyapatite or calcium phosphate, may be applied to the implant surfaces using techniques like plasma spraying or electrophoretic deposition to further encourage bone apposition and accelerate the fusion process.

In another embodiment depicted in FIG. 1-2, for a flexible implant, the algorithm creates two parallel surfaces in the middle of a lofted profile between the endplates to facilitate manufacturing of the central core via injection molding, wherein the flexible core can be made from biocompatible elastomers like silicone or polyurethane and may include embedded fibers or meshes to fine-tune its mechanical properties. The lofted profile may be generated using advanced surface modeling techniques, such as swept surfaces or skinning, to create a smooth, continuous transition between the endplates and the central core. The embedded fibers or meshes within the flexible core may be designed using computational methods, such as topology optimization or reinforcement learning, to achieve the desired balance between flexibility and stability. These fibers or meshes may be made from high-strength, biocompatible materials, such as polyethylene terephthalate (PET) or ultra-high molecular weight polyethylene (UHMWPE), and may be oriented in specific patterns to provide anisotropic mechanical properties that mimic the natural behavior of the intervertebral disc.

In some embodiments, additional features such as fixation points for gripping and inserting the implant, antirotation notches, or radiopaque markers may also be added to the design based on predefined templates or the doctor's specifications. These features may be incorporated into the implant design using parametric modeling techniques, allowing for easy customization and adaptation to the specific surgical requirements. Fixation points, such as threaded holes or undercuts, may be added to the implant to facilitate secure gripping and manipulation during the surgical insertion process. Antirotation notches, such as small protrusions or indentations on the implant surfaces, may be included to prevent undesired rotation or shifting of the implant within the intervertebral space. Radiopaque markers, such as small beads or wires made from high-density materials like tantalum or gold, may be embedded within the implant to enable accurate positioning and monitoring using intraoperative imaging techniques, such as fluoroscopy or computed tomography (CT).

With reference to FIG. 1, the system (100) for designing and manufacturing patient-specific spinal implants may include a remote server (110), a network (160), and a 3D printer (150). In some embodiments, an operator can review and approve the final implant design (126) using the user interface (200) before it is securely transmitted to the 3D printer (150). The user interface (200) interface may provide a user-friendly, interactive platform for visualizing and assessing the final implant design, allowing the operator to examine the implant from various angles, cross-sections, and magnifications. The interface might also include tools for measuring key dimensions, evaluating the fit and alignment of the implant with the patient's anatomy, and simulating the expected biomechanical performance of the implant under different loading conditions. Once the operator is satisfied with the final design, they can provide their approval using secure authentication methods, such as, but not limited to, digital signatures or two-factor authentication, to ensure the integrity and traceability of the approval process.

The 3D printer (150), which may be an industrial-grade additive manufacturing system, including but not limited to an EOS M 290 or Stratasys F900, receives the final implant design (126) from the remote server (110) via the network (160). The network connection between the remote server (110) and the 3D printer (150) can employ secure communication protocols, such as HTTPS or FTPS, to protect the confidentiality and integrity of the transmitted implant design data. The 3D printer (150) is typically located in a dedicated, ISO-certified manufacturing facility with strict quality control and cleanliness standards to ensure the safety and reliability of the produced implants.

The printer then manufactures the patient-specific spinal implant (152) according to the design using biocompatible materials suitable for implantation. The additive manufacturing process may involve advanced techniques, such as powder bed fusion, material jetting, or stereolithography, to build the implant layer by layer with high precision and accuracy. The printer can employ closed-loop control systems, in-process monitoring, and post-process inspection methods to ensure that the manufactured implant meets the specified design tolerances and quality requirements.

In one embodiment, for fusion cages, common materials may include, but are not limited to, titanium alloys like Ti6Al4V, which offer high strength, low density, and excellent osseointegration properties, or polyetheretherketone (PEEK), a radiolucent polymer with mechanical properties similar to cortical bone. These materials can be processed using selective laser melting (SLM) or fused deposition modeling (FDM) techniques, respectively. The SLM process may involve the use of high-powered lasers to selectively melt and fuse thin layers of titanium powder, building the implant from the bottom up with intricate details and fine surface features. The FDM process, on the other hand, might involve the extrusion and deposition of molten PEEK filaments in a layer-by-layer fashion, creating a strong, lightweight implant with good biocompatibility and radiolucency.

According to an embodiment, for flexible core implants, the outer endplates can be 3D printed using titanium or PEEK, while the inner core may be manufactured separately using injection molding and then assembled with the endplates. The injection molding process typically involves the high-pressure injection of molten elastomer into a precision-machined mold cavity, creating a flexible core with the desired shape and mechanical properties. The separately manufactured endplates and core can then be coupled using techniques such as snap-fitting, bonding, or welding to create the final implant. Alternatively, multi-material 3D printing technologies like PolyJet or Digital Light Synthesis (DLS) can be used to fabricate the entire implant in a single process. These technologies enable the simultaneous printing of multiple materials with different properties, allowing for the creation of implants with seamlessly integrated hard and soft components.

Among the materials are biocompatible ceramics such as Zirconia ($ZrO_2$) and Hydroxyapatite through a polymer sintering process. These materials can be printed in a polymer mix which is slightly oversized and then fired at high temp to flash off the polymers and create the final endplates. Polymer can be a typical resin type polymer specially formulated with a mixture of photosensitive resins and a solid load of powder, called slurry. The use of light curing and slurries allows achieving high resolutions and very fine surface roughness in printed products. In addition, it prevents health hazards and (cross-) contamination related to the use of dry powders.

Blending two ceramics to get the final endplate materials can be done in embodiments. This is accomplished by a slurry of these two materials to create a unique ultra strong ceramic which promotes bone growth. The slurry contains UV activated materials which are printed one layer at a time. It is then sintered at high temperature of about 1200-1600 C. This flashes out the polymers to create the final product.

In some embodiments, after printing, the implant (152) undergoes post-processing steps such as support structure removal, surface polishing, and sterilization using methods like gamma irradiation or ethylene oxide (EtO) gas. The finished implant is then packaged and delivered to the hospital for the surgical procedure. The post-processing steps are preferably performed in a controlled, cleanroom environment to minimize the risk of contamination and ensure the highest level of implant quality and safety. Support structure removal may involve the use of specialized tools, such as high-pressure water jets or chemical baths, to carefully detach and remove any temporary supports used during the printing process. Surface polishing can be performed using techniques like mechanical abrasion, electropolishing, or laser polishing to achieve the desired surface finish and smoothness, which can help to reduce friction, wear, and the risk of implant-related complications.

FIG. 2 illustrates a user interface (UI) (200) of the computer-implemented system for planning and simulating a surgical operation to create a patient-specific spinal implant, according to one embodiment. As described in FIG. 1 and as shown in FIG. 2, the UI (200) includes components that allow a user, such as a doctor, to interact with the system via the doctor's computer (130).

In one embodiment, the UI (200) comprises a main viewport (210) that displays a 3D mesh model of the patient's spine (122), generated from patient-specific medical image data by the remote server (110). The main viewport (210) allows the doctor to visualize and manipulate the 3D mesh model (122) in real-time.

A toolbar (220) is provided within the UI (200), which includes various tools and controls for interacting with the 3D mesh model (122). By way of example and not limitation, the toolbar (220) may comprise a visibility toggle button (222) that allows the doctor to selectively show or hide individual vertebral bodies within the 3D mesh model (122), thereby enabling the doctor to focus on specific areas of interest while planning the spinal implant surgery.

The toolbar (220) may also include a transparency adjustment mechanism (224), that allows the doctor to adjust the transparency of the vertebral bodies in the 3D mesh model (122). By increasing transparency, the doctor can better visualize the internal structures and intervertebral spaces, facilitating more accurate planning and placement of the spinal implant.

As depicted in FIG. 2, a segment selection tool (226) is provided in the toolbar (220), which enables the doctor to select and manipulate individual vertebral segments or groups of segments within the 3D mesh model (122). By selecting and adjusting specific segments, the doctor can modify the spacing, tilt, and angles of the intervertebral spaces to achieve the desired spinal curvature and alignment for the patient.

The UI (200) further comprises a warning indicator (230) that displays alerts or warnings if the doctor's adjustments to the 3D mesh model (122) may cause interference with facet joints or other anatomical limitations. The warning indicator (230) helps the doctor to make informed decisions and avoid potential complications during the surgical planning process.

Adjacent to the main viewport (210), the UI (200) includes a 2D view panel (240) that displays traditional 2D views of the patient's CT scans or other medical images. The 2D view panel (240) provides the doctor with additional reference information to complement the 3D mesh model (122) and aids in accurate planning of the spinal implant surgery.

In some cases, the UI (200) also comprises an implant design panel (250) that allows the doctor to select and configure the type of spinal implant to be used in the surgery. The implant design panel (250) may include, but is not limited to, a fusion cage option (252) and a flexible core implant option (254), wherein the doctor can select the desired implant type based on the patient's specific needs and the surgical plan.

Once the doctor has finalized the adjustments to the 3D mesh model (122) and selected the appropriate implant design, an export control (260), such as a button, is provided within the UI (200). Activating the export control (260) transmits the updated 3D mesh model (124) and the chosen implant design parameters back to the remote server (110) for further processing and generation of the final patient-specific spinal implant design (126).

As illustrated in FIG. 1, the UI (200) of the doctor's computer (130) communicates with the remote server (110) via a secure, encrypted connection (162), such as a virtual private network (VPN) or encrypted tunnel. This ensures the protection of sensitive patient data during the transfer of information between the doctor's computer (130) and the remote server (110).

Figure 3:
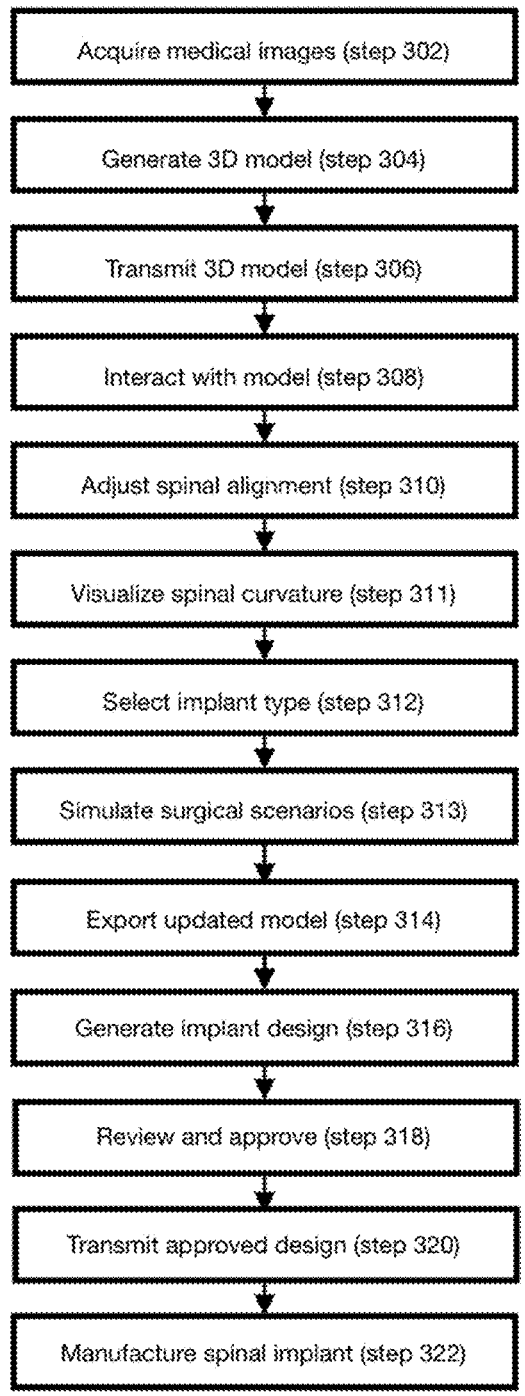
FIG. 3 is a flow diagram illustrating the system and user workflow for planning and simulating a surgical operation to create a patient-specific spinal implant using the computer-implemented system, according to one embodiment of the present invention.

FIG. 3 is a flow diagram illustrating, by way of example and not limitation, the system and user workflow for planning and simulating a surgical operation to create a patient-specific spinal implant using the computer-implemented system (100) described in FIG. 1 and the user interface (200) depicted in FIG. 2.

In one embodiment, the workflow typically begins with the acquisition of patient-specific medical image data (step 302) from an MRI, CT scan, or 3D scanning system (102), wherein the image data is transmitted to the remote server (110) via the network (160) and stored in the database (116).

In one embodiment, the one or more processors (112) of the remote server (110) generally execute the first algorithm (123) stored in the memory (114) to generate a 3D mesh model (122) of the patient's spine (step 304), wherein the algorithm preprocesses the image data by automatically detecting and removing artifacts and noise, smoothing the vertebral surfaces, separating individual vertebral bodies, and creating reference lines and connection points.

In another embodiment, the generated 3D mesh model (122) is then optionally transmitted to the doctor's computer (130) via the secure, encrypted connection (162) (step 306), and the one or more processors (132) of the doctor's computer (130) display the 3D mesh model (122) on the main viewport (210) of the user interface (200).

As depicted in FIG. 3, the doctor can interact with the 3D mesh model (122) using the tools provided in the toolbar (220) of the UI (200) (step 308), wherein the doctor may toggle the visibility of individual vertebral bodies using the visibility toggle button (222), adjust the transparency of the vertebral bodies using the transparency toggle (224), and select and manipulate specific vertebral segments or groups using the segment selection tool (226).

In one embodiment, as the doctor adjusts the spacing, tilt, and angles of the intervertebral spaces to achieve the desired spinal curvature and alignment (step 310), the warning indicator (230) can display alerts if the adjustments may cause interference with facet joints or other anatomical limitations, and the doctor might also refer to the traditional 2D views of the patient's CT scans or medical images displayed in the 2D view panel (240) to aid in accurate planning.

An algorithm is capable of sub pixel calculations in an embodiment of the present invention which can determine more precisely the shape of the 2D layers of bone vs noise by looking pixel to pixel to calculate the gradient. The intensity of one pixel to the next determines the edge. It is possible to accurately calculate the resolution in this way. Sometimes the edges can be fuzzy and this can add precision. For example, if the intensity of one pixel is 100 and the other is 15, the theoretical portion is shifted slightly toward the pure white pixel using statistical positioning of a virtual pixels for the actual edge.

In one embodiment, when updating the 3D mesh model (122), the system employs advanced image analysis techniques to automatically detect the center of each vertebral body and create a curved line connecting these centers, thereby visualizing the overall spinal curvature (step 311). This visual representation allows the doctor to intuitively assess the patient's spinal alignment and identify areas requiring adjustment. Furthermore, the user interface (200) provides an intuitive way for the doctor to grab and manipulate individual vertebral segments or groups of segments using the segment selection tool (226), enabling them to simulate various surgical scenarios and view the potential impact on adjacent non-surgical levels in real-time (step 313). This interactive feature enhances the doctor's ability to make informed decisions and optimize the surgical plan based on the patient's unique anatomy and biomechanics.

According to an embodiment, once the doctor has substantially finalized the adjustments to the 3D mesh model (122), they select the desired spinal implant type (fusion cage (252) or flexible core implant (254)) using the implant design panel (250) (step 312), and the doctor then clicks the export button (260) to transmit the updated 3D mesh model (124) and chosen implant design parameters back to the remote server (110) (step 314).

The one or more processors (112) of the remote server (110) receive the updated 3D mesh model (124) and execute additional algorithms to generate the final patient-specific spinal implant design (126) (step 316), wherein for a fusion cage, the algorithm generates an extrusion base template from the surface-mapped endplates, while for a flexible implant, it creates generally parallel surfaces in the middle of a lofted profile to facilitate manufacturing, but it is understood in the art that such values may change per configuration of the device in different settings.

In another embodiment, an operator reviews and approves the final implant design (126) (step 318), and upon approval, the final implant design (126) is transmitted to the 3D printer (150) via the network (160) (step 320).

Finally, the 3D printer (150) receives the final implant design (126) and manufactures the patient-specific spinal implant (152) using biocompatible materials suitable for implantation (step 322), thereby providing the manufactured implant (152) ready for use in the patient's spinal surgery.

In one embodiment, throughout the workflow, the system leverages computer-aided planning, modeling, and simulation technologies to create a highly customized spinal implant that substantially matches the unique anatomy of the patient's spine, wherein the user interface (200) enables the doctor to interact with the 3D mesh model (122), make precise adjustments, and select the appropriate implant design, while the remote server (110) handles the complex data processing, model generation, and implant design tasks, and the 3D printer (150) fabricates the final patient-specific implant (152).

The system can reside in a cloud server or remote server, and the system can be trained on one model. Over time as more images are created the system will learn and the predictive ability will improve. For example, a portal can be provided where patients can load up CT Scan data and get a 3D model output. That model can be exported to patients as an STL file that they can print themselves on a printer and bring to their doctor for discussion. This data provides the necessary feedback to improve model precision. If a problem is found the system is retrained and retains the first training model to better predict the proper outputs.

The embodiments described herein are given for the purpose of facilitating the understanding of the present invention and are not intended to limit the interpretation of the present invention. The respective elements and their arrangements, materials, conditions, shapes, sizes, or the like of the embodiment are not limited to the illustrated examples but may be appropriately changed. Further, the constituents described in the embodiment may be partially replaced or combined together.

What is claimed is:

1. A computer-implemented method for planning and simulating a surgical operation to create a patient-specific spinal implant, comprising:
    receiving, by one or more processor, patient-specific medical image data from an MRI, CT, or 3D scanning system;
    automatically detecting and removing unwanted artifacts and noise using a secondary filtering comprising one or more of median filtering, Gaussian smoothing, or anisotropic diffusion;
    generating, by the one or more processors, a 3D mesh model of the patient's spine, including individual vertebral bodies and intervertebral spaces, by converting the received image data using a first algorithm stored in a memory;

separating the individual vertebral bodies for independent manipulation by applying image segmentation techniques comprising one or more of thresholding, region growing, or active contours, wherein each vertebra is assigned a unique label or identifier to facilitate subsequent referencing and selection;

smoothing the surfaces of the segmented vertebral bodies using one or more of Laplacian smoothing or Taubin smoothing to reduce staircase artifacts;

creating reference lines and connection points on the vertebral models to aid in the placement and orientation of the spinal implant, wherein these include one or more anatomical landmarks selected from pedicles, transverse processes, or superior and inferior endplates;

transmitting, by the one or more processors, the 3D mesh model represented as a high-resolution polygon mesh defining the surface geometry of the vertebrae, wherein the polygon mesh data structure allows for efficient manipulation and rendering of the complex vertebral shapes to a remote doctor's computer for real-time manipulation;

receiving, by the one or more processors, input from the doctor to control the visibility and transparency of individual vertebral bodies to adjust the spacing, tilt, and angles of one or more intervertebral spaces to achieve a desired spinal curvature;

updating, by the one or more processors, the 3D mesh model based on the doctor's input;

generating, by the one or more processors, a final 3D spinal implant design based on the updated 3D mesh model, wherein the implant design comprises surface-mapped endplates that match the anatomy of the patient's vertebral bodies;

transmitting, by the one or more processors, the final implant design to a 3D printer for manufacturing; and manufacturing the patient-specific spinal implant according to the design using biocompatible materials suitable for implantation.

2. The method of claim 1, wherein generating the 3D mesh model further comprises: automatically detecting and removing unwanted artifacts comprising streak artifacts in CT scans caused by metallic implants using a metal artifact reduction (MAR) algorithm and noise from the medical image data using a secondary algorithm stored in the memory; and smoothing the surfaces of the vertebral bodies for improved accuracy.

3. The method of claim 1, wherein receiving input from the doctor further comprises: providing an interface that allows the doctor to toggle the visibility and transparency of individual vertebral bodies in the 3D mesh model; and displaying warning indicators if the doctor's adjustments may cause interference in the facet joints or other limitations.

4. The method of claim 1, wherein updating the 3D mesh model further comprises: automatically detecting the center of each vertebral body and creating a curved line connecting the centers to visualize the spinal curvature; and allowing the doctor to grab and adjust individual segments or groups of segments to view the impact on adjacent non-surgical levels.

5. The method of claim 1, wherein generating the final 3D spinal implant design further comprises: creating an extrusion base template from the surface-mapped endplates to form a flat parallel surface or solid extrusion profile matching the patient's vertebral body surfaces.

6. The method of claim 5, further comprising: providing the doctor with an option to select either a fusion cage design or a flexible core implant design; and generating the selected design by filling the space between the surface-mapped endplates with the appropriate material.

7. The method of claim 6, wherein generating the flexible core implant design further comprises: creating two parallel surfaces in the middle of the lofted profile to facilitate manufacturing of the central flexible core through an injection molding process.

8. The method of claim 1, wherein the final implant design further comprises: one or more fixation points on the implant surface for gripping and inserting the implant into the patient's body.

9. The method of claim 1, further comprising: transmitting the 3D mesh model and the final implant design between the one or more processors and the remote doctor's computer via a secure VPN or encrypted tunnel for review and approval.

10. A computer-implemented method for planning and simulating a surgical operation to create a patient-specific spinal implant, comprising:

receiving, by one or more processors, patient-specific medical image data from an MRI, CT scan, or 3D scanning system;

automatically detecting and removing unwanted artifacts and noise using a secondary filtering process comprising one or more of median filtering, Gaussian smoothing, or anisotropic diffusion;

generating, by the one or more processors, a 3D mesh model of the patient's spine, including individual vertebral bodies and intervertebral spaces, by converting the received image data using a first algorithm stored in memory;

separating individual vertebral bodies for independent, remote manipulation, wherein each vertebra is assigned a unique identifier to facilitate selection, and wherein the system enables precise real-time control over vertebral spacing, tilt, and angle;

smoothing the surfaces of the separated vertebral bodies using one or more of Laplacian smoothing or Taubin smoothing to reduce staircase artifacts;

creating reference lines and connection points on the vertebral models automatically detected using machine learning algorithms trained on a large dataset of annotated spinal images to aid in the placement and orientation of the spinal implant, wherein these include one or more anatomical landmarks selected from pedicles, transverse processes, or superior and inferior endplates;

transmitting, by the one or more processors, the 3D mesh model represented as a high-resolution polygon mesh defining the surface geometry of the vertebrae, wherein the polygon mesh data structure allows for efficient remote manipulation and real-time adjustment of individual vertebrae by a surgeon;

receiving, by the one or more processors, input from the doctor to adjust visibility, transparency, and the positioning of individual vertebrae, modifying spacing, tilt, and angle to achieve a custom spinal alignment for the implant;

updating, by the one or more processors, the 3D mesh model dynamically based on the surgeon's real-time input, ensuring accurate adjustments before implant design;

generating, by the one or more processors, a final 3D spinal implant design based on the updated 3D model, wherein the implant comprises surface-mapped endplates that precisely match the anatomy of the patient's vertebral bodies;

transmitting, by the one or more processors, the final implant design to a 3D printer for manufacturing; and manufacturing the patient-specific spinal implant according to the design using biocompatible materials suitable for implantation.

11. The method of claim 10, wherein the generated final spinal implant design uses a fusion cage extrusion base template from the surface-mapped endplates to form a flat parallel surface or solid extrusion profile matching the vertebral body surfaces.

* * * * *